Oct. 25, 1938. M. H. HORVATH Plant Pat. 297
ROSE
Filed Sept. 1, 1937
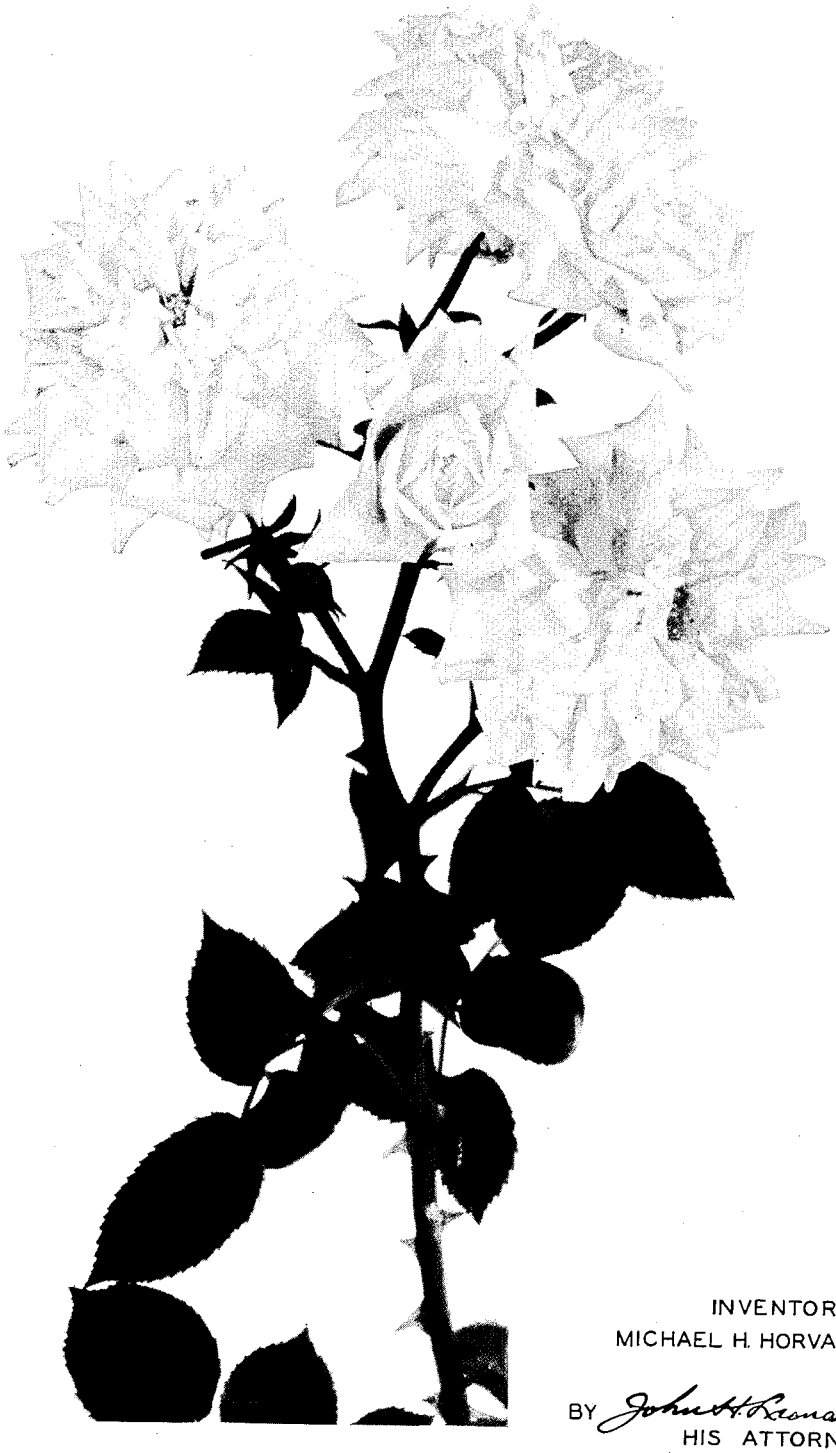
INVENTOR
MICHAEL H. HORVATH
BY John H. Barnard
HIS ATTORNEY Patented Oct. 25, 1938 Plant Pat. 297

UNITED STATES PATENT OFFICE

297

ROSE

Michael H. Horvath, Mentor, Ohio

Application September 1, 1937, Serial No. 162,064

1 Claim. (Cl. 47—61)

This invention relates to a new variety of rose, a "Rose Setigera Hybrid," produced by crossing a variety, "Mrs. F. F. Prentiss," as the female parent, with a variety, "Souv. de Georges Pernet," as the male parent. Asexual reproduction has been made in considerable quantities.

The variety, being a "Rosa Setigera Hybrid," has its hardy characteristics, and it is grown in the temperate region without protection and can be grown sucessfully with protection in the colder regions where growing of roses has been impossible or exceedingly difficult.

The shrub grows to an ultimate height of two feet, with a spread of six to eight feet or more, space permitting, and it is preeminently fit for ground covering because of its decumbent and spreading mat-like characteristics.

My new rose has a rich and clean foliage of a bottle green color corresponding to Maerz and Paul Plate No. 31 J—7, which foliage is strongly resistant to ordinary rose maladies. The flowers are arranged in panicle formation from common glabrous peduncles, and they are of a distinctive peach blossom color Plate No. 1 C—2 having a reflex color, comparable to Plate No. 11 A—1, with a center of an orange undertone, comparable to "Capucine", Plate No. 9 I—8. Some fifty to sixty petals of a sharp recurving and imbricating nature make up each flower.

The variety is characteristically a persistent grower and bloomer, the blooming period beginning in June and lasting until frost, during which time flowers are produced in large quantities and of a character excellent for cutting and decorative work.

The drawing further illustrates many of the characteristics which are not found in the parent stock and which make the variety of more value as a shrub and enhance its beauty.

The following is a detailed description of my new variety:

Parentage:

*Seedling.*—Seed parent—Setigera Hybrid—Mrs. F. F. Prentiss. Pollen parent—Souv. de Georges Pernet.

Classification:

*Botanic and commercial.*—Setigera Hybrid.

*Flower*

Blooming habit:

Location where observations were made—trial field of Michael H. Horvath, at Mentor, Ohio.

Recurrent—perpetual flowering.

Bud:

*Size.*—Moderate—medium.

*Form.*—Globular—unaffected by weather.

*Color.*—When sepals first divide—peach blossom. When petals begin to unfurl—peach blossom. When half blown—peach blossom.

*Sepals.*—Smooth—curl back.

*Calyx.*—Shape—round. Size—medium. Aspect—smooth. Odor when rubbed—none.

*Peduncle.*—Length—2–2½ inches. Aspect—prickly. Color—medium green. Strength—moderate but ample.

*Opening.*—Opens well in all weather conditions.

Bloom:

*Size.*—Medium size.

*Borne.*—Singly and in threes.

*Stems.*—Medium, slender.

*Form.*—When first open—semi-globular. Permanence—good until ready to shed.

*Petalage.*—Number of petals under normal conditions—50–60:

*Color.*—Center of flower—peach blossom. Outer petals—peach blossom. Base of petals—undertone of orange. Inside of petals—peach blossom. Reverse of petals—peach blossom. General tonality from a distance—peach blossom having reflex comparable to Maerz & Paul Plate No. 11 A—1.

*Variegations.*—None.

*Discoloration.*—General tonality at end of first and second days—holds color well to the end. Third day—holds color well to the end.

Petals:

*Texture.*—Medium thickness.

*Form.*—Semi-globular.

*Arrangement.*—Imbricated.

*Petaloids in center.*—None.

*Persistence.*—Drop cleanly.

*Fragrance.*—Moderate briar scent.

*Nature.*—Regular—briarlike.

*Lasting quality.*—On the plant and as cut flower—good on the plant or cut.

Genital organs:

*Stamens.*—Few.

*Color.*—Orange.

*Arrangement.*—Regular.

*Stamens, filaments (threads).*—Short.

*Color.*—White.

*Pollen.*—Orange.

*Styles.*—Loosely arranged.

*Stigmas.*—White.

*Ovaries.*—None—plant entirely sterile.

Fruit:
*Variety.*—None
*Form.*—

*Plant*

Form: Semi-prostrate spreading bush.
Growth: Strong.
Foliage: Small with seven leaflets.
*Size.*—Small.
*Quantity.*—Ample.
*Color.*—New foliage: upper side—meadow green. Under side—lighter green. Old foliage—bottle green.
*Shape.*—Ovate—pointed.
*Texture.*—Upper side—glossy. Under side—smooth. Ribs and veins—insignificant.
*Edge.*—Serrated.
*Serration.*—Regular.
*Rachis.*—Smooth. Color—green. Underside—same.
*Stipules.*—Medium—smooth.
*Disease resistance.*—Resistant.
Wood:
*New wood.*—Color—green with reddish shading. Bark—smooth.
*Old wood.*—Color—bottle green. Bark—bottle green.
Thorns (thorns are divided into thorns, prickles and short needles):
*Quantity.*—On main stalks from base—abundant. On laterals from stalk—abundant.
*Form.*—Wide base with downward slant.
*Color when young.*—Reddish.
*Position.*—Irregularly distributed.
*Prickles.*—Abundant on lateral growth.
*Short needles.*—Abundant on lateral growth.

Having now fully shown and described my new rose, and the mode of its production, what I claim and desire to secure by Letters Patent of the United States, is:

A rose as herein shown and described and distinguished by the shrub of a hardy character and growing persistently throughout the growing period in a manner preeminently fit for ground covering, rich and clean bottle-green foliage resistant to rose maladies, distinctive peach blossom flowers having a reflex as disclosed and a center of an orange undertone, distinctive sharp recurving and imbricating petals, the perpetual floriferous character, and the flower and prolific petal growth and quality making them excellent for cutting and decorative work.

MICHAEL H. HORVATH.